(12) United States Patent
Hanselmann et al.

(10) Patent No.: US 7,358,393 B2
(45) Date of Patent: Apr. 15, 2008

(54) METHOD FOR PREPARING β-ALANINAMIDES

(75) Inventors: Paul Hanselmann, Glis (CH); Stefan Hildbrand, Riehen (CH)

(73) Assignee: Lonza Ltd., Basel (CH)

( * ) Notice: Subject to any disclaimer, the term of this patent is extended or adjusted under 35 U.S.C. 154(b) by 435 days.

(21) Appl. No.: 10/488,692

(22) PCT Filed: Sep. 4, 2002

(86) PCT No.: PCT/EP02/09893

§ 371 (c)(1),
(2), (4) Date: Mar. 5, 2004

(87) PCT Pub. No.: WO03/022795

PCT Pub. Date: Mar. 20, 2003

(65) Prior Publication Data

US 2004/0220410 A1 Nov. 4, 2004

Related U.S. Application Data

(60) Provisional application No. 60/332,547, filed on Nov. 26, 2001.

(30) Foreign Application Priority Data

Sep. 6, 2001 (EP) .................................. 01121342

(51) Int. Cl.
C07D 233/64 (2006.01)
C07D 231/02 (2006.01)
(52) U.S. Cl. ..................... 564/126; 548/338.1
(58) Field of Classification Search .............. 548/336.1
See application file for complete search history.

(56) References Cited

U.S. PATENT DOCUMENTS

| 4,313,894 A | * | 2/1982 | Kleemann et al. .......... 558/341 |
| 4,359,416 A | | 11/1982 | Vinick |
| 5,037,849 A | * | 8/1991 | Simon et al. ............... 514/509 |
| 5,561,110 A | | 10/1996 | Michaelis et al. |
| 5,792,771 A | * | 8/1998 | App et al. ................ 514/266.3 |
| 5,792,784 A | | 8/1998 | Seguin et al. |
| 6,037,440 A | * | 3/2000 | Wilson et al. .............. 528/243 |
| 6,280,715 B1 | | 8/2001 | Seguin et al. |

FOREIGN PATENT DOCUMENTS

| DE | 2429927 A | * | 1/1975 |
| EP | 0294668 | | 12/1988 |
| JP | 06247850 A | * | 9/1994 |
| WO | WO 91-05555 | | 5/1991 |
| WO | WO 01-64638 | | 9/2001 |

OTHER PUBLICATIONS

Schaper, W., Synthesis, vol. 9, (1985), pp. 861-867.
Andreae, S., et al. Liebigs Ann. Chem., vol. 3, (1992), pp. 239-256.
Database Crossfire Beilstein 'Online!, Beilstein Institut zur Förderung der Chemischen Wissenschaften, XFIRE, database accession No. br 222197, XP002224290, (Beilstein '290), (1988).
Cossey, A.L., et al., Aust. J. Chem., vol. 29, (1976), pp. 1039-1050.
Database Crossfire Beilstein 'Online!, Beilstein Institut zur Förderung der Chemischen Wissenschaften, XFIRE, Database accession No. br 774851, XP002224292, (1976).
Norman, R.O.C., "Principles of Organic Synthesis", p. 572, London, (1976).
Osdene, T.S., et al., J. Med. Chem., vol. 10, (1967), pp. 165-171.
Shukla, J.S., et al., J. Indian Chem. Soc., vol. 55, (1978), pp. 281-283.
Leonard et al. J. Amer. Chem. Soc., vol. 72, (1950), pp. 2980-2984.
Database Crossfire Beilstein 'Online!, Beilstein Institut zur Förderung der Chemischen Wissenschaften, XFIRE, Database accession No. rid 663077, XP002224294, (1950).
Database Crossfire Beilstein 'Online!, Beilstein Institut zur Förderung der Chemischen Wissenschaften, XFIRE, Database accession No. rid 630250, XP002224293, (1978).
Bowman et al., J. Chem. Soc., (1954), pp. 1171-1176.
Database Crossfire Beilstein 'Online!, Beilstein Institut zur Förderung der Chemischen Wissenschaften, XFIRE, Database accession No. rid 68295, XP002224295, (1954).
Database Crossfire Beilstein 'Online!, Beilstein Institut zur Förderung der Chemischen Wissenschaften, XFIRE, Database accession No. br 395823, XP002224291, (1985).

* cited by examiner

Primary Examiner—Rebecca Anderson
Assistant Examiner—Michael P. Barker
(74) Attorney, Agent, or Firm—Fisher, Christen & Sabol

(57) ABSTRACT

The invention relates to β-alanine amides of general formula (I), wherein: $R^1$ represents hydrogen or $C_{1-6}$ alkyl that is optionally substituted by hydroxy, amino, carboxy, carbamoyl, methylmercapto, guanidino, optionally substituted aryl or heteroaryl, and; $R^2$ represents hydrogen or $R^1$ and $R^2$, together, form a group of formula $-(CH_2)_n-$, wherein n is 3 or 4. Said β-alanine amides are produced without using an amino protective group by reacting the corresponding amine with a cyanoacetic ester in order to form an acetamide and by effecting a subsequent catalytic hydrogenation. The method is suited, in particular, for producing carcinine (β-alanyl-histamine, R?1 ¿=imidazol-4-ylmethyl, $R^2$=H), a naturally occurring pseudo dipeptide, which is used as an active ingredient having an antioxidative effect in medicaments and cosmetics.

10 Claims, No Drawings

METHOD FOR PREPARING β-ALANINAMIDES

This is a 371 national stage application of PCT/EP02/09893, filed on Sep. 4, 2002 that has benefit of U.S. Provisional Application Ser. No. 60/332,547, filed on Nov. 26, 2001, and that has priority benefit of European Patent Application No. 01121342.8, filed on Sep. 6, 2001.

The present invention relates to a method for preparing amides of β-alanine, in particular pseudodipeptides such as, for example, carcinine. It furthermore relates to novel cyanoacetamides as intermediates in the method of the invention.

Carcinine (β-alanylhistamine) is a naturally occurring pseudodipeptide of the structure below, which can be isolated from animal tissue. Carcinine has an antioxidative action and has been proposed as drug for certain complications of diabetes (U.S. Pat. No. 5,561,110), in particular cataract (U.S. Pat. No. 5,792,784), and as component of cosmetic preparations (U.S. Pat. No. 6,280,715).

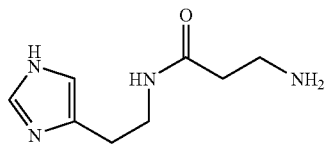

Carcinine

The known syntheses of carcinine from the components histamine and β-alanine require the use of protective groups and/or activated derivatives and are therefore not very suitable for the inexpensive preparation of large amounts.

It was therefore an object of the present invention to provide a method suitable for the technical synthesis of carcinine and other pseudodipeptides of β-alanine, which does not require the use of protective groups or expensive derivatives and which uses only readily accessible starting materials.

According to the invention, this object is achieved by the method of the invention.

The β-alaninamides which can be produced according to the invention have the general formula

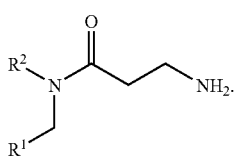

Here, $R^1$ is hydrogen or $C_{1-6}$-alkyl which is unsubstituted or substituted with hydroxy, amino, carboxy, carbamoyl, methylmercapto, guanidino, unsubstituted or substituted aryl or heteroaryl and $R^2$ is hydrogen, or $R^1$ and $R^2$ together form a group of the formula —$(CH_2)_n$— where n is 3 or 4.

These compounds may be present in a neutral form or, after protonation of the primary amino group, as salts with acids. Some of the compounds, in particular those containing imidazolyl radicals, may also be present in a plurality of tautomeric forms or as a mixture of such forms.

Here and below, $C_{1-6}$-alkyl means all linear or branched primary, secondary or tertiary alkyl groups having from 1 to 6 carbon atoms, i.e. for example methyl, ethyl, propyl, isopropyl, butyl, sec-butyl, tert-butyl, iso-butyl, pentyl, iso-pentyl, neopentyl, 2-methylbutyl, hexyl, 2-methylpentyl, 3-methylpentyl etc. This applies accordingly to $C_{1-10}$-alkyl, in which case, for example, groups such as octyl or 2-ethylhexyl are also included in addition to the groups already mentioned.

Aryl means mono- or polycyclic carbocyclic aromatic groups such as, in particular, phenyl or naphthyl and, accordingly, heteroaryl means mono- or polycyclic heterocyclic aromatic groups having one or more heteroatoms, in particular imidazolyl or indolyl. Where appropriate, aryl groups may also have one or more of the abovementioned substituents, in particular hydroxyl groups as in 4-hydroxyphenyl, for example.

It has been found that amines of the general formula

in which $R^1$ and $R^2$ are as defined above, can be reacted with a cyanoacetic ester of the general formula

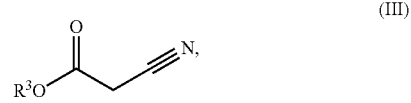

in which $R^3$ is $C_{1-10}$-alkyl, to give a cyanoacetamide of the general formula

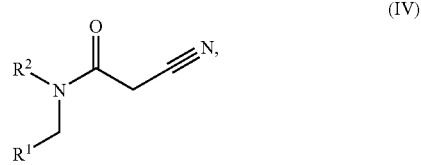

in which $R^1$ and $R^2$ are as defined above, or a corresponding salt, and the cyanoacetamide (IV) can be converted to the target compound (I) or a corresponding salt by catalytic hydrogenation.

$R^1$ is preferably hydrogen or unsubstituted or substituted $C_{1-4}$-alkyl, in particular methyl, isopropyl, isobutyl, sec-butyl, indol-3-ylmethyl, benzyl, p-hydroxybenzyl, 2-(methylsulfanyl)ethyl, hydroxymethyl, 1-hydroxyethyl, carbamoylmethyl, 2-carbamoyl-ethyl, carboxymethyl, 2-carboxyethyl, 4-aminobutyl or 3-guanidinopropyl.

$R^2$ is preferably hydrogen.

Particularly preferably, $R^1$ is imidazol-4-ylmethyl or 3-methylimidazol-4-ylmethyl and $R^2$ is hydrogen.

$R^3$ is preferably methyl or ethyl.

If the amine (II) is present as a salt in which the primary amino group is protonated, the latter must first be deprotonated by adding a base. Bases which may be used here are in principle all bases which are more basic than the primary amino group. Preference is given to using a medium-strength to strong base. Examples of compounds suitable for this are alkali metal hydroxides such as sodium or potassium hydroxide, tertiary amines such as triethylamine, 4-dimethylaminopyridine, 1,4-diaza[2.2.2]bicyclooctane, bicyclic amidines ("DBN", "DBU") and, in nonaqueous solvents, alkali metal alkoxides such as sodium methoxide or sodium ethoxide and, in aprotic solvents, also alkali metal hydrides and amides, such as, for example, sodium hydride or sodium amide. The base is preferably used in stoichiometric or nearly stoichiometric amounts.

Preferred solvents for the first stage are polar protic or aprotic solvents such as water, $C_{1-4}$-alkanols such as, for example, methanol or ethanol and amides such as, for example, N,N-dimethylformamide, N,N-dimethyl-acetamide, 1-methyl-2-pyrrolidone or 1,3-dimethyl-3,4,5,6-tetrahydro-2(1H)-pyrimidinone (DMPU).

Preferred catalysts used for the hydrogenation are metal catalysts based on nickel, cobalt, copper, rhodium, palladium, ruthenium or platinum, which are, where appropriate, applied to a support. These include, for example, nickel and cobalt catalysts of the Raney type, finely divided platinum (obtained, for example, by reduction of $PtO_2$), rhodium, palladium or platinum on activated carbon or aluminum oxide or cobalt on silicon dioxide (silica).

Particular preference is given to Raney nickel and Raney cobalt and to rhodium on activated carbon or aluminum oxide.

Solvents which may be used in the hydrogenation are the usual solvents for hydrogenation of nitriles to amines, such as, for example, water, concentrated aqueous ammonia solution, methanol, ethanol, N,N-dimethyl-formamide or mixtures of said solvents.

The cyanoacetamides of the general formula

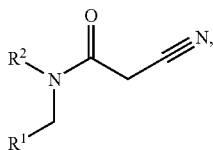

(IV)

in which $R^1$ and $R^2$ are as defined above, and the salts thereof are novel and are likewise subject matter of the invention.

Preference is given to those cyanoacetamides (IV) in which $R^1$ is unsubstituted or substituted imidazol-4-ylmethyl and $R^2$ is hydrogen. Examples of suitable substituents here are $C_{1-6}$-alkyl groups, in particular methyl.

Particularly preferred cyanoacetamides (IV) are N-(cyanoacetyl)histamine of the formula

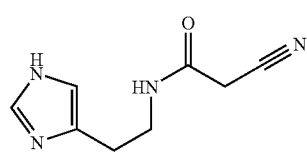

and the salts and tautomers thereof and also N-(cyanoacetyl)-3-methylhistamine of the formula

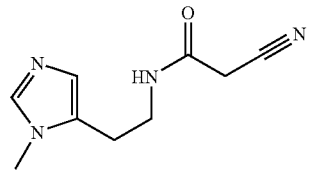

and the salts thereof.

The following examples illustrate the carrying-out of the method of the invention and the preparation of the compounds of the invention and are not to be regarded as being limiting.

EXAMPLE 1

2-Cyano-N-[2-(1(3)H-imidazol-4-yl)ethyl]acetamide (N-cyanoacetylhistamine)

7.60 g (67.2 mmol) of ethyl cyanoacetate were added dropwise at 60° C. to a solution of 5.00 g (45 mmol) of histamine in 50 g of ethanol. After 2 h at 80° C., the reaction mixture was concentrated in a rotary evaporator and the residue was purified by means of flash column chromatography on silica gel (eluent: ethyl acetate→ethyl acetate/methanol 1:1 gradient).

Yield: 6.61 g (82%) $^1$H-NMR (DMSO-$d_6$, 400 MHz): δ=11.8 (br., 1H); 8.28 (t, 1H), 7.52 (s, 1H); 6.80 (s, 1H); 3.60 (s, 2H); 3.30 (q, 2H); 2.65 (t, 2H).

$^{13}$C NMR (DMSO-$d_6$, 100 MHz): δ=161.92; 134.63; 134.21; 116.64; 116.13; 39.25; 26.63; 25.23.

LC-MS: m/z=179 ([M+H]$^+$), 161, 149, 138, 112, 95, 83.

EXAMPLE 2

3-Amino-N-[2-(1H-imidazol-4-yl-ethyl]propionamide (β-alanylhistamine, carcinine)

92 mg of Rh/Al$_2$O$_3$ (5% Rh) were added to a solution of 1.00 g (5.61 mmol) of 2-cyano-N-[2-(1(3)H-imidazol-4-yl)ethyl]acetamide (prepared according to example 1) in 11.4 g of ethanol and 7.6 g of concentrated aqueous ammonia solution. The mixture was hydrogenated at 90° C. and a hydrogen pressure of 50 bar for 2 h. The catalyst was filtered off via Celite® and the filtrate was concentrated in a rotary evaporator. After drying at 50° C./20 mbar for a relatively long time, 0.89 g of crude carcinine with a content (HPLC) of 73% was obtained.

$^1$H-NMR (DMSO-$d_6$, 400 MHz): δ=12 (br., 1H); 7.95 (t, 1H), 7.50 (s, 1H); 6.77 (s, 1H); 3.6 (br., 1H); 3.25 (q, 2H); 2.74 (t, 2H); 2.63 (t, 2H); 2.15 (t, 2H). LC-MS: m/z=183 ([M+H]$^+$), 166, 148, 124, 95.

The invention claimed is:

1. A method for preparing β-alaninamides of the formula:

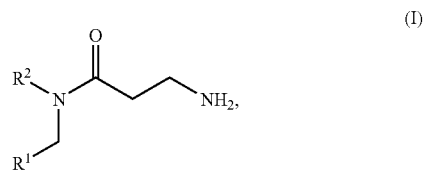

(I)

in which
  (i) $R^1$ is hydrogen or $C_{1-6}$-alkyl that is unsubstituted or substituted with hydroxy, amino, carboxy, carbamoyl, methylmercapto, guanidino or unsubstituted or substituted aryl or heteroaryl, and $R^2$ is hydrogen, or
  (ii) $R^1$ and $R^2$ together form a group of the formula —$(CH_2)_n$— where n is 3 or 4, comprising, in a first stage, reacting an amine of the formula:

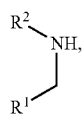
(II)

in which $R^1$ and $R^2$ are as defined above, or a corresponding salt, with a cyanoacetic ester of the formula:

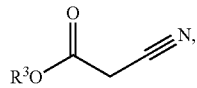
(III)

in which $R^3$ is $C_{1-10}$-alkyl, in a solvent selected from the group consisting of ethanol, N,N-dimethyformamide and mixtures thereof, to give a cyanoacetamide of the formula:

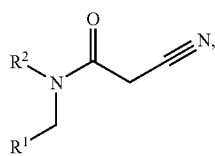
(IV)

in which $R^1$ and $R^2$ are as defined above, or a corresponding salt, and, in a second stage, converting the cyanoacetamide of formula (IV), or a corresponding salt, by catalytic hydrogenation to the compound (I), or a corresponding salt.

2. A method for preparing β-alaninamides of the formula:

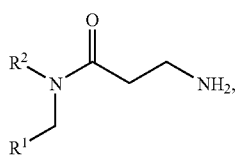
(I)

in which
  (i) $R^1$ is unsubstituted or substituted imidazol-4-ylmethyl, and (ii) $R^2$ is hydrogen, comprising, in a first stage, reacting an amine of the formula:

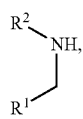
(II)

in which $R^1$ and $R^2$ are as defined above, or a corresponding salt, with a cyanoacetic ester of the formula:

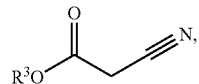
(III)

in which $R^3$ is $C_{1-10}$-alkyl, to give a cyanoacetamide of the formula:

(IV)

in which $R^1$ and $R^2$ are as defined above, or a corresponding salt, and, in a second stage, converting the cyanoacetamide of formula (IV), or a corresponding salt, by catalytic hydrogenation to the compound (I), or a corresponding salt.

3. The method as clamed in claim 2 wherein the catalyst used is the second stage is selected from the group consisting of rhodium on activated carbon, rhodium on aluminum oxide, Raney nickel and Raney cobalt.

4. N-(Cyanoacetyl) histamine of the formula:

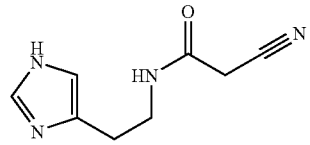

or a salt thereof or a tautomer thereof.

5. N-(Cyanoacetyl)-3-methylhistamine of the formula:

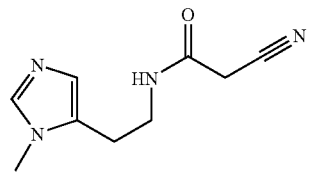

or a salt thereof.

6. The method as claimed in claim 1, wherein the catalyst used in the second stage is selected from the group consisting of rhodium on activated carbon, rhodium on aluminum oxide, Raney nickel and Raney cobalt.

7. The method as claimed in claim 2, wherein the catalyst used in the second stage is selected from the group consisting of rhodium on activated carbon, rhodium on aluminum oxide, Raney nickel and Raney cobalt.

8. A cyanoacetamide of the formula:
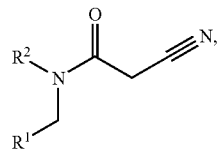
(IV)
in which
(i) $R^1$ is unsubstituted or substituted imidazol-4-ylmethyl and (ii) $R^2$ is hydrogen.
9. The method as claimed in claim 2, wherein $R^1$ is unsubstituted imadazol-4-ylmethyl.
10. The cyanoacetoamide (IV) as claimed in claim 8, wherein $R^1$ is unsubstituted imadazol-4-ylmethyl and $R^2$ is hydrogen.
* * * * *